(12) United States Patent
Trotta

(10) Patent No.: US 10,794,841 B2
(45) Date of Patent: Oct. 6, 2020

(54) COMPOSITE MATERIAL STRUCTURE MONITORING SYSTEM

(71) Applicant: Infineon Technologies AG, Neubiberg (DE)

(72) Inventor: Saverio Trotta, Munich (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 283 days.

(21) Appl. No.: 15/973,099

(22) Filed: May 7, 2018

(65) Prior Publication Data

US 2019/0339214 A1    Nov. 7, 2019

(51) Int. Cl.
*G01N 22/02* (2006.01)
*B62D 29/04* (2006.01)
*B62D 63/04* (2006.01)

(52) U.S. Cl.
CPC .......... *G01N 22/02* (2013.01); *B62D 29/041* (2013.01); *B62D 63/04* (2013.01); *G01N 2223/052* (2013.01); *G01N 2223/615* (2013.01)

(58) Field of Classification Search
CPC ....... G01N 22/02; B62D 29/041; B62D 63/04
See application file for complete search history.

(56) References Cited

U.S. PATENT DOCUMENTS

| | | | |
|---|---|---|---|
| 4,241,347 A | 12/1980 | Albanese et al. | |
| 6,147,572 A | 11/2000 | Kaminski et al. | |
| 6,414,631 B1 | 7/2002 | Fujimoto | |
| 6,636,174 B2 | 10/2003 | Arikan et al. | |
| 7,048,973 B2 | 5/2006 | Sakamoto et al. | |
| 7,057,564 B2 | 6/2006 | Tsai et al. | |
| 7,171,052 B2 | 1/2007 | Park | |
| 7,317,417 B2 | 1/2008 | Arikan et al. | |
| 7,596,241 B2 | 9/2009 | Rittscher et al. | |
| 7,692,574 B2 | 4/2010 | Nakagawa | |
| 7,873,326 B2 | 1/2011 | Sadr | |
| 7,889,147 B2 | 2/2011 | Tam et al. | |
| 8,228,382 B2 | 7/2012 | Pattikonda | |
| 8,497,805 B2 | 7/2013 | Rofougaran et al. | |
| 8,659,369 B2 | 2/2014 | Rofougaran et al. | |

(Continued)

FOREIGN PATENT DOCUMENTS

| | | |
|---|---|---|
| CN | 1463161 A | 12/2003 |
| CN | 203950036 U | 11/2004 |

(Continued)

OTHER PUBLICATIONS

Richards, Mark A., "Fundamentals of Radar Signal Processing," McGraw Hill Electronic Engineering, ISBN: 0-07-144474-2, Jun. 2005, 93 pages.

(Continued)

*Primary Examiner* — Marc Anthony Armand
(74) *Attorney, Agent, or Firm* — Slater Matsil, LLP

(57) ABSTRACT

A method for monitoring property changes in a composite material structure includes: transmitting a radio-frequency (RF) signal towards the composite material structure using a millimeter-wave radar sensor embedded in the composite material structure; receiving a reflected signal from the composite material structure using the millimeter-wave radar sensor; processing the reflected signal; and determining a property change in the composite material structure based on processing the reflected signal.

25 Claims, 5 Drawing Sheets

(56) References Cited

U.S. PATENT DOCUMENTS

| | | |
|---|---|---|
| 8,731,502 B2 | 5/2014 | Salle et al. |
| 8,836,596 B2 | 9/2014 | Richards et al. |
| 8,847,814 B2 | 9/2014 | Himmelstoss et al. |
| 8,860,532 B2 | 10/2014 | Gong et al. |
| 8,976,061 B2 | 3/2015 | Chowdhury |
| 9,172,132 B2 | 10/2015 | Kam et al. |
| 9,182,476 B2 | 11/2015 | Wintermantel |
| 9,202,105 B1 | 12/2015 | Wang et al. |
| 9,413,079 B2 | 8/2016 | Kamgaing et al. |
| 9,495,600 B2 | 11/2016 | Heu et al. |
| 2002/0189336 A1 | 12/2002 | McEwan |
| 2003/0179127 A1 | 9/2003 | Wienand |
| 2004/0238857 A1 | 12/2004 | Beroz et al. |
| 2006/0001572 A1 | 1/2006 | Gaucher et al. |
| 2006/0049995 A1 | 3/2006 | Imaoka et al. |
| 2006/0067456 A1 | 3/2006 | Ku et al. |
| 2007/0210959 A1 | 9/2007 | Herd et al. |
| 2008/0106460 A1 | 5/2008 | Kurtz et al. |
| 2008/0238759 A1 | 10/2008 | Carocari et al. |
| 2008/0291115 A1 | 11/2008 | Doan et al. |
| 2008/0308917 A1 | 12/2008 | Pressel et al. |
| 2009/0073026 A1 | 3/2009 | Nakagawa |
| 2009/0085815 A1 | 4/2009 | Jakab et al. |
| 2009/0153428 A1 | 6/2009 | Rofougaran et al. |
| 2009/0315761 A1 | 12/2009 | Walter et al. |
| 2010/0207805 A1 | 8/2010 | Haworth |
| 2011/0299433 A1 | 12/2011 | Darabi et al. |
| 2012/0087230 A1 | 4/2012 | Guo et al. |
| 2012/0092284 A1 | 4/2012 | Rofougaran et al. |
| 2012/0116231 A1 | 5/2012 | Liao et al. |
| 2012/0195161 A1 | 8/2012 | Little et al. |
| 2012/0206339 A1 | 8/2012 | Dahl |
| 2012/0265486 A1 | 10/2012 | Klofer et al. |
| 2012/0268314 A1 | 10/2012 | Kuwahara et al. |
| 2012/0280900 A1 | 11/2012 | Wang et al. |
| 2013/0027240 A1 | 1/2013 | Chowdhury |
| 2013/0106673 A1 | 5/2013 | McCormack et al. |
| 2013/0139596 A1* | 6/2013 | Lowe .................. G01N 22/02 73/582 |
| 2014/0028542 A1 | 1/2014 | Lovitt et al. |
| 2014/0070994 A1 | 3/2014 | Schmalenberg et al. |
| 2014/0145883 A1 | 5/2014 | Baks et al. |
| 2014/0324888 A1 | 10/2014 | Xie et al. |
| 2015/0051874 A1 | 2/2015 | Bommer et al. |
| 2015/0181840 A1 | 7/2015 | Tupin, Jr. et al. |
| 2015/0185316 A1 | 7/2015 | Rao et al. |
| 2015/0212198 A1 | 7/2015 | Nishio et al. |
| 2015/0243575 A1 | 8/2015 | Strothmann et al. |
| 2015/0277569 A1 | 10/2015 | Sprenger et al. |
| 2015/0325925 A1 | 11/2015 | Kamgaing et al. |
| 2015/0346820 A1 | 12/2015 | Poupyrev et al. |
| 2015/0348821 A1 | 12/2015 | Iwanaga et al. |
| 2015/0364816 A1 | 12/2015 | Murugan et al. |
| 2016/0018511 A1 | 1/2016 | Nayyar et al. |
| 2016/0041617 A1 | 2/2016 | Poupyrev |
| 2016/0041618 A1 | 2/2016 | Poupyrev |
| 2016/0061942 A1 | 3/2016 | Rao et al. |
| 2016/0061947 A1 | 3/2016 | Patole et al. |
| 2016/0098089 A1 | 4/2016 | Poupyrev |
| 2016/0103213 A1 | 4/2016 | Ikram et al. |
| 2016/0109566 A1 | 4/2016 | Liu et al. |
| 2016/0118353 A1 | 4/2016 | Ahrens et al. |
| 2016/0135655 A1 | 5/2016 | Ahn et al. |
| 2016/0146931 A1 | 5/2016 | Rao et al. |
| 2016/0146933 A1 | 5/2016 | Rao et al. |
| 2016/0187462 A1 | 6/2016 | Altus et al. |
| 2016/0191232 A1 | 6/2016 | Subburaj et al. |
| 2016/0223651 A1 | 8/2016 | Kamo et al. |
| 2016/0240907 A1 | 8/2016 | Haroun |
| 2016/0249133 A1 | 8/2016 | Sorensen |
| 2016/0252607 A1 | 9/2016 | Saboo et al. |
| 2016/0259037 A1 | 9/2016 | Molchanov et al. |
| 2016/0266233 A1 | 9/2016 | Mansour |
| 2016/0269815 A1 | 9/2016 | Liao et al. |
| 2016/0291130 A1 | 10/2016 | Ginsburg et al. |
| 2016/0298957 A1* | 10/2016 | Little, Jr. .............. G01N 22/00 |
| 2016/0299215 A1 | 10/2016 | Dandu et al. |
| 2016/0306034 A1 | 10/2016 | Trotta et al. |
| 2016/0320852 A1 | 11/2016 | Poupyrev |
| 2016/0320853 A1 | 11/2016 | Lien et al. |
| 2016/0327633 A1 | 11/2016 | Kumar Y.B. et al. |
| 2016/0334502 A1 | 11/2016 | Ali et al. |
| 2016/0349845 A1 | 12/2016 | Poupyrev et al. |
| 2017/0033062 A1 | 2/2017 | Liu et al. |
| 2017/0045607 A1 | 2/2017 | Bharadwaj et al. |
| 2017/0052618 A1 | 2/2017 | Lee et al. |
| 2017/0054449 A1 | 2/2017 | Mani et al. |
| 2017/0060254 A1 | 3/2017 | Molchanov et al. |
| 2017/0070952 A1 | 3/2017 | Balakrishnan et al. |
| 2017/0074974 A1 | 3/2017 | Rao et al. |
| 2017/0074980 A1 | 3/2017 | Adib et al. |
| 2017/0090014 A1 | 3/2017 | Subburaj et al. |
| 2017/0090015 A1 | 3/2017 | Breen et al. |
| 2017/0115377 A1 | 4/2017 | Giannini et al. |
| 2017/0131395 A1 | 5/2017 | Reynolds et al. |
| 2017/0139036 A1 | 5/2017 | Nayyar et al. |
| 2017/0141453 A1 | 5/2017 | Waelde et al. |
| 2017/0170947 A1 | 6/2017 | Yang |
| 2017/0176574 A1 | 6/2017 | Eswaran et al. |
| 2017/0192847 A1 | 7/2017 | Rao et al. |
| 2017/0201019 A1 | 7/2017 | Trotta |
| 2017/0212597 A1 | 7/2017 | Mishra |
| 2017/0361662 A1 | 12/2017 | Wei et al. |
| 2017/0364160 A1 | 12/2017 | Malysa et al. |
| 2018/0046255 A1 | 2/2018 | Rothera et al. |
| 2018/0101239 A1 | 4/2018 | Yin et al. |

FOREIGN PATENT DOCUMENTS

| | | |
|---|---|---|
| CN | 1716695 A | 1/2006 |
| CN | 101490578 A | 7/2009 |
| CN | 101585361 A | 11/2009 |
| CN | 102788969 A | 11/2012 |
| CN | 102967854 A | 3/2013 |
| CN | 103529444 A | 1/2014 |
| DE | 102008054570 A1 | 6/2010 |
| DE | 102011100907 A1 | 1/2012 |
| DE | 102011075725 A1 | 11/2012 |
| DE | 102014118063 A1 | 7/2015 |
| EP | 2341332 A1 | 6/2011 |
| GB | 2247799 A | 3/1992 |
| JP | 2001174539 A | 6/2001 |
| JP | 2004198312 A | 7/2004 |
| JP | 2006234513 A | 9/2006 |
| JP | 2008029025 A | 2/2008 |
| JP | 2008089614 A | 4/2008 |
| JP | 2009069124 A | 4/2009 |
| JP | 2011529181 A | 12/2011 |
| JP | 2012112861 A | 6/2012 |
| JP | 2013521508 A | 6/2013 |
| JP | 2014055957 A | 3/2014 |
| KR | 20090063166 A | 6/2009 |
| KR | 20140082815 A | 7/2014 |
| WO | 2007060069 A1 | 5/2007 |
| WO | 2013009473 A2 | 1/2013 |
| WO | 2016033361 A1 | 3/2016 |

OTHER PUBLICATIONS

Schemmel, P., et al., "Monitorning stress changes in carbon fiber reinforced polymer composites with GHz radiation" Institure of Photonics and Quantum Sciences, Heriot-Watt University, Edinburgh, UK, vol. 56, No. 22, Aug. 1, 2017, pp. 6405-6409.

Chen, Xiaolong et a., "Detection and Extraction of Marine Target with Micromotion via Short-Time Fractional Fourier Transform in Sparse Domain," IEEE International Conference on Signal Processing, Communications and Computing, ICSPCC, Aug. 5-8, 2016, 5 pages.

Chen, Xiaolong et al., "Detection and Extraction of Target with Micromotion in Spiky Sea Clutter via Short-Time Fractional Fourier Transform", IEEE Transactions on Geoscience and Remote Sensing, vol. 52, No. 2, Feb. 2014, pp. 1002-1018.

(56) References Cited

OTHER PUBLICATIONS

Chuanhua, Du "Chinese Doctoral Dissertations & Master's Theses Full Text Database (Masters)—Information Science and Technology Series," China National Knowledge Infrastructure, ISSN 1674-0246, CN 11-9144/G, Dec. 16, 2004-Mar. 2015, 14 pages.

Deacon, Peter et al., "Frequency Modulated Continuous Wave (FMCW) Radar," Design Team 6 Technical Lecture, Nov. 9, 2011, 27 pages.

Diederichs, Kailtyn et al., "Wireless Biometric Individual Identification Utilizing Millimeter Waves", IEEE Sensors Council, 3500104, vol. 1, No. 1, Feb. 2017, 4 pages.

Dooring Alert Systems, "Dooring Alert Systems Riders Matter" http:\\dooringalertsystems.com, printed Oct. 4, 2017, 16 pages.

Filippelli, Mario et al., "Respiratory dynamics during laughter," J Appl Physiol, (90), 1441-1446, Apr. 2001, http://jap.physiology.org/content/jap/90/4/1441.full.pdf.

Fox, Ben "The Simple Technique That Could Save Cyclists' Lives," https://www.outsideonline.com/2115116/simple-technique-could-save-cyclists-lives, Sep. 19, 2016, 6 pages.

Gu, Changzhan et al., "Assessment of Human Respiration Patterns via Noncontact Sensing Using Doppler Multi Radar System", Sensors Mar. 2015, 15(3), 6383-6398, doi: 10.3390/s150306383, 17 pages.

Guercan, Yalin "Super-resolution Algorithms for Joint Range-Azimuth-Doppler Estimation in Automotive Radars," Technische Universitet Delft, TUDelft University of Technology Challenge the Future, Jan. 25, 2017, 72 pages.

Inac, Ozgur et al., "A Phased Array RFIC with Built-In Self-Test Capabilities," IEEE Transactions on Microwave Theory and Techniques, vol. 60, No. 1, Jan. 2012, 10 pages.

Kizhakkel, V., "Pulsed Radar Target Recognition Based on Micro-Doppler Signatures Using Wavelet Analysis", A Thesis, Graduate Program in Electrical and Computer Engineering, Ohio State University, Jan. 2013-May 2013, 18 pages.

Kuehnke, Lutz, "Phased Array Calibration Procedures Based on Measured Element Patterns," 2001 Eleventh International Conference on Antennas and Propagation, IEEE Conf., Publ. No. 480, Apr. 17-20, 2001, 4 pages.

Lim, Soo-Chul et al., "Expansion of Smartwatch Touch Interface from Touchscreen to Around Device Interface Using Infrared Line Image Sensors," Sensors, ISSN 1424-8220, vol. 15, 16642-16653, doi:10.3390/s150716642, www.mdpi.com/journal/sensors, Jul. 15, 2009, 12 pages.

Lin, Jau-Jr et al., "Design of an FMCW radar baseband signal processing system for automotive application," SpringerPlus a SpringerOpen Journal, (2016) 5:42, http://creativecommons.org/licenses/by/4.0/, DOI 10.1186/s40064-015-1583-5; Jan. 2016, 16 pages.

Microwave Journal Frequency Matters, "Single-Chip 24 GHz Radar Front End," Infineon Technologies AG, www.microwavejournal.com/articles/print/21553-single-chip-24-ghz-radar-front-end, Feb. 13, 2014, 2 pages.

Simon, W., et al., "Highly Integrated KA-Band Tx Frontend Module Including 8x8 Antenna Array," IMST GmbH, Germany, Asia Pacific Microwave Conference, Dec. 7-10, 2009, 63 pages.

Suleymanov, Suleyman "Design and Implementation of an FMCW Radar Signal Processing Module for Automotive Applications," Master Thesis, University of Twente, Aug. 31, 2016, 61 pages.

Thayananthan, T. et al., "Intelligent target recognition using micro-doppler radar signatures," Defence R&D Canada, Radar Sensor Technology III, Proc. Of SPIE, vol. 7308, 730817, Dec. 9, 2009, 11 pages.

Thayaparan, T. et al. "Micro-Doppler Radar Signatures for Intelligent Target Recognition," Defence Research and Development Canada, Technical Memorandum, DRDC Ottawa TM 2004-170, Sep. 2004, 73 pages.

Wilder, Carol N., et al., "Respiratory patterns in infant cry," Canada Journal of Speech, Human Communication Winter, 1974-75, http://cjslpa.ca/files/1974_HumComm_Vol_01/No_03_2-60/Wilder_Baken_HumComm_1974.pdf, pp. 18-34.

Xin, Qin et al., "Signal Processing for Digital Beamforming FMCW SAR," Hindawi Publishing Corporation, Mathematical Problems in Engineering, vol. 2014, Article ID 859890, http://dx.doi.org/10.1155/2014/859890, 11 pages.

Schroff, Florian et al., "FaceNet: A Unified Embedding for Face Recognition and Clustering," CVF, CVPR2015, IEEE Computer Society Conference on Computer Vision and Pattern Recognition; Mar. 12, 2015, pp. 815-823.

Infineon, "Using BGT24MTR11 in Low Power Applications", BGT24MTR11, 24 Ghz Radar, RF and Protection Devices, Application Note AN341, Revision: Rev. 1.0, Dec. 2, 2013, 25 pages.

Texas Instruments, "XWR1xxx Power Management Optimizations—Low Cost LC Filter Solution", Application Report SWRA577—Oct. 2017, 19 pages.

Texas Instruments, "Programming Chirp Parameters in TI Radar Devices", Application Report SWRA553—May 2017, 15 pages.

R. Matsuzaki et al., "Antenna/sensor multifunctional composites for the wireless detection of damage," Composites Science and Technology, Dec. 2009, pp. 2507-2513, vol. 69, Issues 15-16, Science Direct.

Q. Ye et al., "Review on Composite Structural Health Monitoring Based on Fiber Bragg Grating Sensing Principle," Journal of Shanghai Jiaotong University (Science), Apr. 2013, pp. 129-139, vol. 18, Issue 2, Springer Link.

\* cited by examiner

COMPOSITE MATERIAL STRUCTURE MONITORING SYSTEM

TECHNICAL FIELD

The present invention relates generally to an electronic system, and, in particular embodiments, to a composite material monitoring system.

BACKGROUND

Vehicles, such as cars, have improved fuel efficiency in the past few years. Regardless of the technology of the car (e.g., combustion engine, electric car, or hybrid), improved efficiency is typically desirable. For example, improved efficiency typically results in an increase in driving range. A reduction in operating costs may also be achieved, for example, as a result of reduced consumption of fuel. Improvements in fuel efficiency may also contribute to a less harmful impact to the environment.

The efficiency of cars may be improved in a variety of ways. For example, the car engine may be designed to improve efficiency or car's aerodynamic design may be modified to improve efficiency. Another way to improve efficiency is to reduce the weight of the car.

A way to reduce the weight of the car is to use lightweight materials to make, for example, the frame of the car. Usage of lightweight materials, such as composite materials, is therefore desirable. Usage of composite materials, such as carbon fiber, in the production of frames of cars, bikes, motor bikes, buses, and trains is expected to increase in the future. For example, FIG. 1A shows an example of a car using a carbon fiber frame. FIG. 1B shows an example of a carbon fiber bicycle.

Among the reasons for the increase in popularity of composite materials in the production of frames are that composite materials are typically strong and lightweight. For example, FIG. 1C shows an example of a carbon fiber frame of a car being lifted by two humans.

SUMMARY

In accordance with an embodiment, a method for monitoring property changes in a composite material structure includes: transmitting a radio-frequency (RF) signal towards the composite material structure using a millimeter-wave radar sensor embedded in the composite material structure; receiving a reflected signal from the composite material structure using the millimeter-wave radar sensor; processing the reflected signal; and determining a property change in the composite material structure based on processing the reflected signal.

In accordance with another embodiment, a system includes a plurality of sensing devices disposed in a composite material structure and a central processor. Each sensing device of the plurality of sensing devices includes: a millimeter-wave radar sensor circuit configured to transmit an RF signal towards the composite material structure, and after transmitting the RF signal, receive an echo signal from the composite material structure, and a respective controller, where the respective controller or the central processor is configured to: process the echo signal, and determine a property change in the composite material structure based on processing the echo signal.

In accordance with yet another embodiment, a car includes: a carbon fiber frame; a main central processing unit (CPU); and a plurality of sensing devices embedded in the carbon fiber frame. Each sensing device of the plurality of sensing devices includes: a millimeter-wave radar sensor circuit configured to: transmit a plurality of RF signals towards the carbon fiber frame, and receive a plurality of echo signals from the carbon fiber frame, and a respective controller, where the respective controller or the main CPU is configured to: process each of the plurality of the echo signals; and determine a property change in the carbon fiber frame based on processing each of the plurality of the echo signals.

BRIEF DESCRIPTION OF THE DRAWINGS

For a more complete understanding of the present invention, and the advantages thereof, reference is now made to the following descriptions taken in conjunction with the accompanying drawings, in which.

Figure 1A:
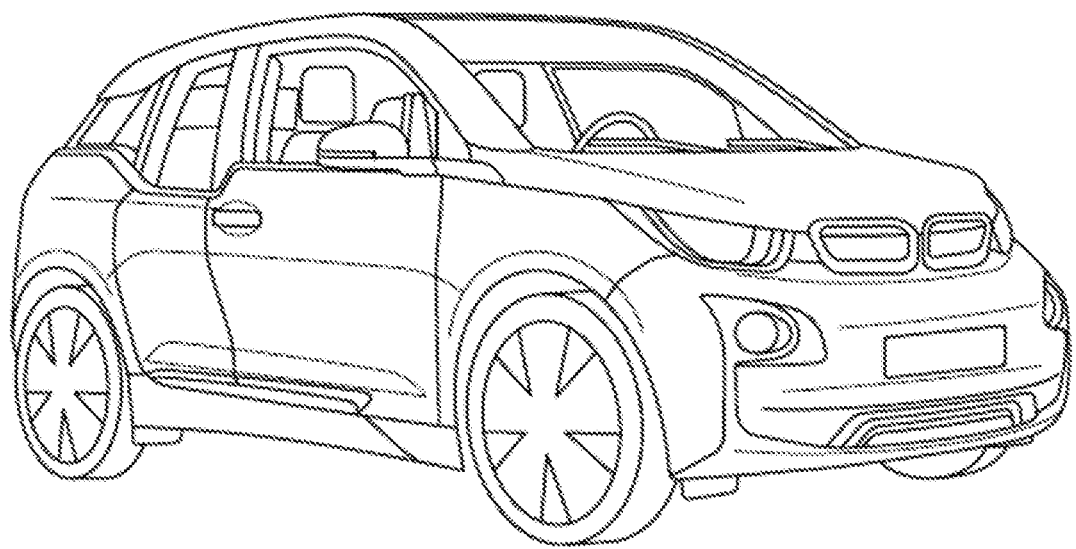
FIGS. 1A-1C show examples of carbon fiber frames.
Figure 1B:
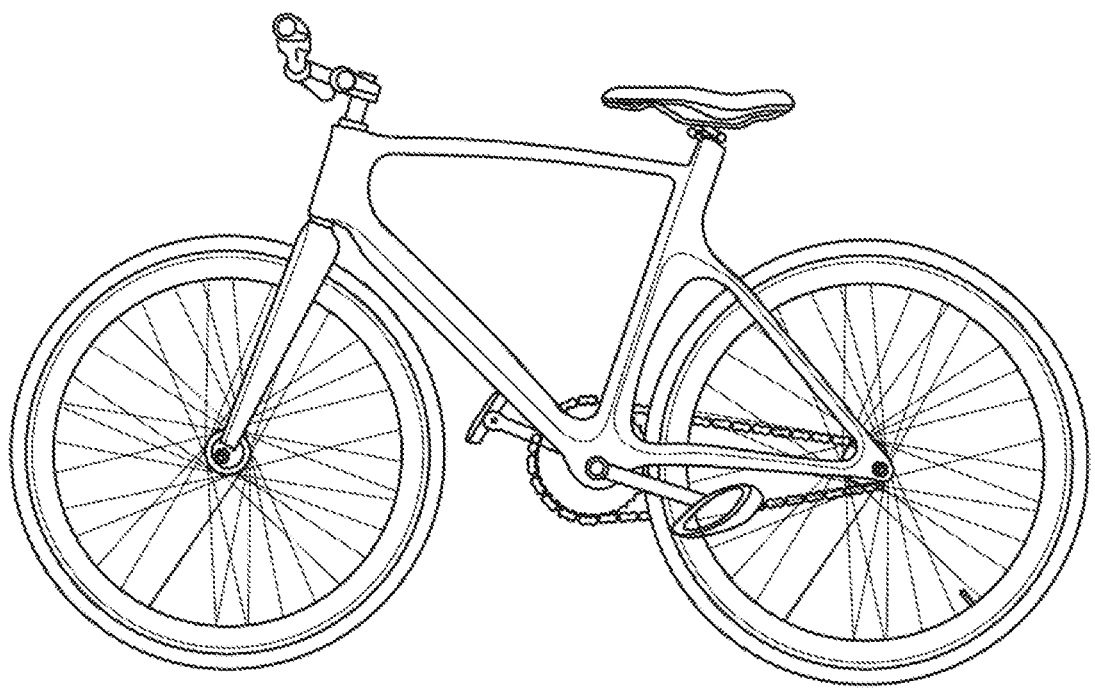
Figure 1C:
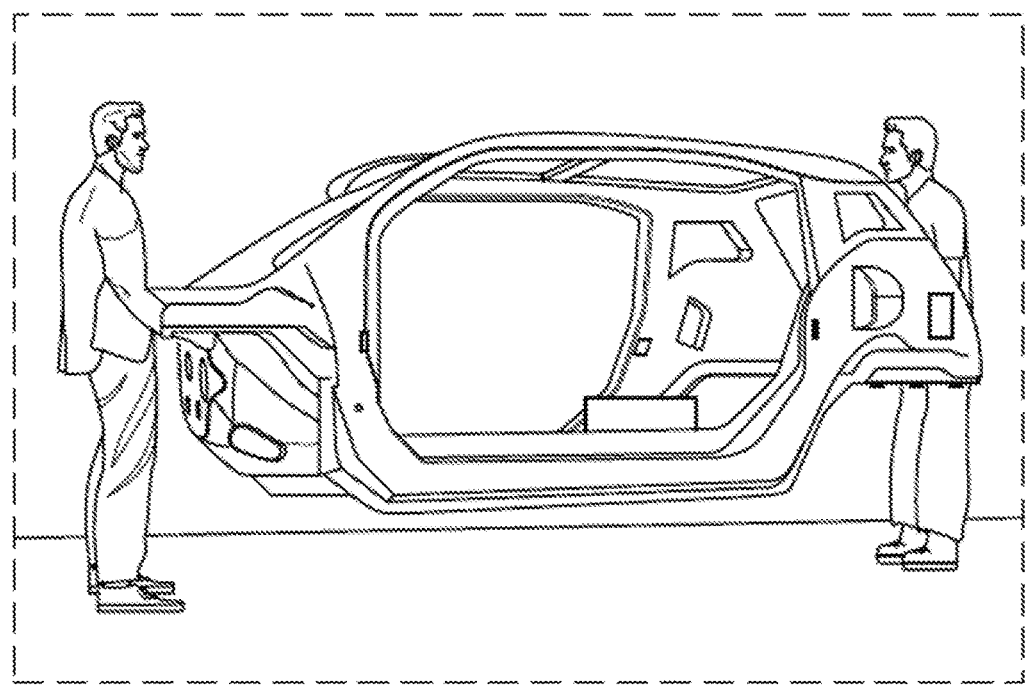

Corresponding numerals and symbols in different figures generally refer to corresponding parts unless otherwise indicated. The figures are drawn to clearly illustrate the relevant aspects of the preferred embodiments and are not necessarily drawn to scale. To more clearly illustrate certain embodiments, a letter indicating variations of the same structure, material, or process step may follow a figure number.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The description below illustrates the various specific details to provide an in-depth understanding of several example embodiments according to the description. The embodiments may be obtained without one or more of the specific details, or with other methods, components, materials and the like. In other cases, known structures, materials or operations are not shown or described in detail so as not to obscure the different aspects of the embodiments. References to "an embodiment" in this description indicate that a particular configuration, structure or feature described in relation to the embodiment is included in at least one embodiment. Consequently, phrases such as "in one embodiment" that may appear at different points of the present description do not necessarily refer exactly to the same embodiment. Furthermore, specific formations, structures or features may be combined in any appropriate manner in one or more embodiments.

The present invention will be described with respect to embodiments in a specific context, a system for monitoring the change in properties of composite materials in a frame of a car. Embodiments of the present invention may be used in other types of vehicles, such as buses, trains, motor bikes, and bicycles or other types of composite material structures, such as a composite material construction crane. Embodiments may also be used in other system where monitoring the change in properties of a composite material structure is desirable.

The properties of composite materials, such as carbon fiber, may change over time. For example, long term stress (e.g., compressive force, vibration, etc.) may result in delamination, deformation, cracks, or loss of stiffness. The permittivity of the composite material, also referred to as $\varepsilon_r$, may also change over time. In some cases, temporary stress, such as a car tire hitting a structural failure in a road surface (e.g., a pothole) may produce sufficient stress to cause a change in the properties of the composite material.

In a car having a frame that is made with composite material, changes in the properties of the composite material of the frame may result in failure. For example, the composite material may lose elasticity over time (e.g., as a result of various stresses). The loss of elasticity of the composite material may make the composite material structure more susceptible to crack in response to various stresses, such as hitting a pothole with the car.

Monitoring the property changes of the composite material of the frame and determining whether a property of the composite material has changed is, therefore, advantageous. For example, by monitoring the property changes of the composite material, it is possible to determine whether the composite material structure is close to cracking.

Changes in the composite material properties may result in specific signatures detectable by illuminating the composite material and analyzing the reflected echo signal. For example, the average reflected power of GHz illumination from the surface of carbon fiber reinforced polymer (CFRP) composite is linearly related to the stress of the material.

In an embodiment of the present invention, a millimeter-wave radar embedded in a composite material structure is used to detect property changes of the composite material structure by comparing measurements of the phase of the echo signal with an initial phase measurements and/or by comparing measurements of the average power of the echo signal with an initial average reflected power. In some embodiments, the property changes of the composite material that are monitored include delamination, deformation, and permittivity of the composite material.

Figure 2:
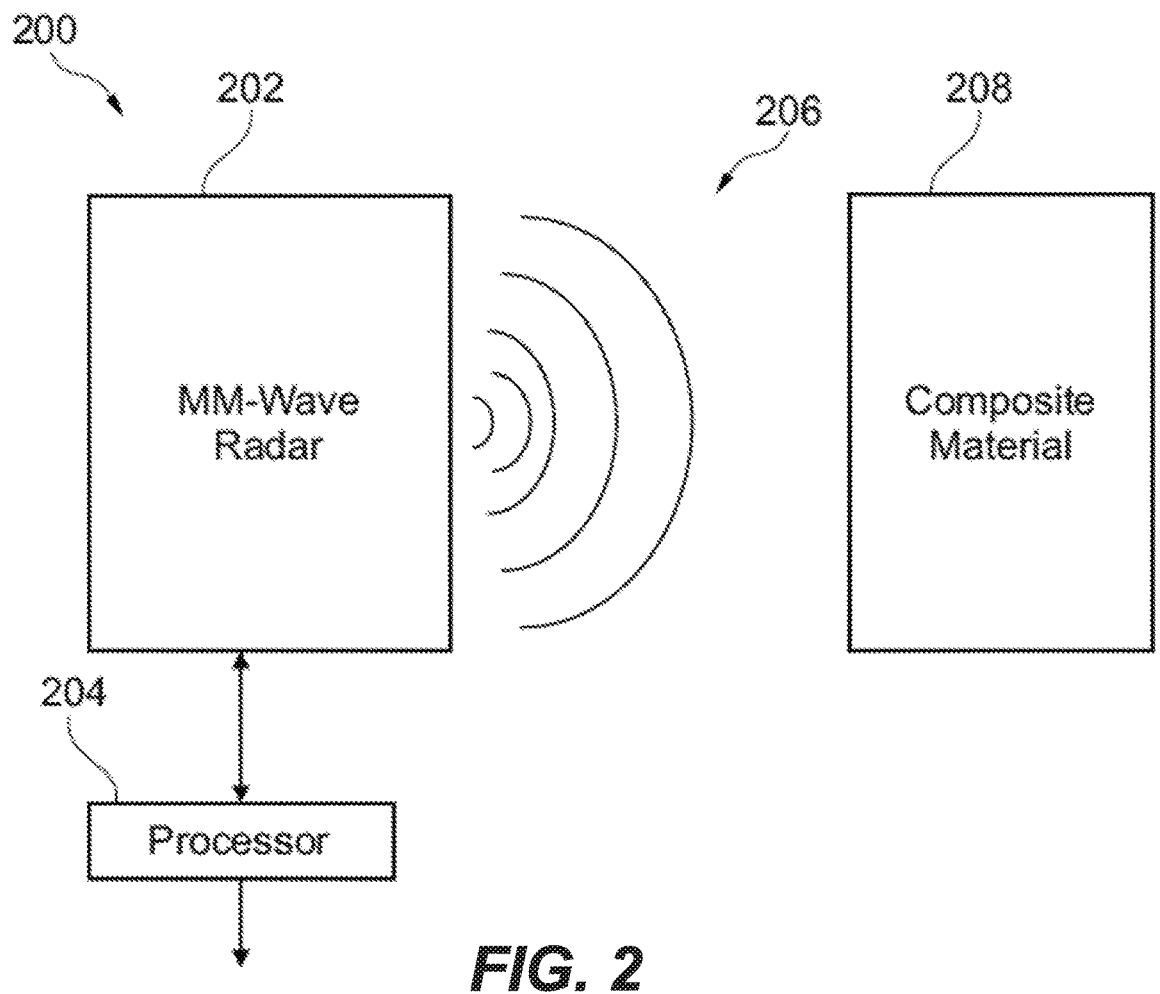
FIG. 2 shows a millimeter-wave radar system, according an embodiment of the present invention.

Embodiments of the present invention detect property changes (e.g., deformation, delamination, changes in permittivity, etc.) of a composite material of a frame of a car by using a millimeter-wave radar together with signal processing techniques. For example, FIG. 2 shows millimeter-wave radar system 200, according an embodiment of the present invention. Millimeter-wave radar system 200 includes millimeter-wave radar 202 and processor 204.

During normal operation, millimeter-wave radar 202 transmits one or more radiation pulses 206, such as chirps, towards composite material 208. The transmitted radiation pulses 206 are reflected by composite material 208. The reflected radiation pulses (not shown in FIG. 2), which are also referred to as the reflected signals or the echo signals, are detected by millimeter-wave radar 202, digitized, thereby generating echo data, and processed by processor 204 to, for example, identify property changes in composite material structure 208.

Processor 204 analyses the echo data to determine whether a change in properties of the composite material structure has occurred. More particularly, processor 204 determines whether such a change has occurred based on the difference between the reflected signal and an expected signal which is indicative of the frame of the car (for instance, of a specific region of the structure which has generated the reflected signal) being in good state (i.e., undamaged). Here, "difference" is understood as a discrepancy or deviation between the reflected signal and the expected signal. In effect, the difference may take the form of one or more quantitative parameter indicative of a gap between the two signals. For instance, in some embodiments a parameter indicative of a phase difference between the signals may be used. In other embodiments, a parameter indicative of a difference in the respective powers of the signals may be used. Using a parameter constructed as a function of other such parameters such as a weighted combination thereof, and the like, may also be used.

For example, processor 204 may analyze the phase of the echo signal and compare the phase to a phase reference to determine whether the composite material structure has changed. For example, at a first time (e.g., during manufacturing or assembly), a first phase measurement is performed and stored. Since the distance between the millimeter-wave radar 202 and composite material structure 208 does not change during normal operation, any subsequent phase measurement is expected to be equal to the first, or expected, measurement. If a subsequent phase measurement is different that the first measurement, such change in phase is indicative that a change in the properties of the composite material structure (e.g., delamination, deformation, displacement, etc.) has occurred. For example, a change in the permittivity $\varepsilon_r$ of the composite material may result in a bubble that deforms the composite material structure. Such deformation changes the distance between composite material structure 208 and millimeter-wave radar 202. Millimeter-wave radar 202 detects such change in distance by detecting a change in the subsequent phase measurement.

As another example, processor 204 may analyze the average power of the echo signal and compare the average power to an average power reference to determine whether the composite material has changed. For example, at a first time (e.g., during manufacturing or assembly), a first average power measurement is performed and stored. Absent a change in the properties of the composite material structure, any subsequent average power measurement is expected to be equal to the first measurement. If a subsequent average power measurement is different than the first measurement, such change in average power is indicative that a change in the properties of the composite material (e.g., loss of strength) has occurred.

Processor 204 may be implemented as a general purpose processor, controller or digital signal processor (DSP), such as a low power general purpose microcontroller. In some embodiments, processor 204 may be implemented as a custom application specific integrated circuit (ASIC). In some embodiments, processor 204 includes a plurality of processors, each having one or more processing cores. In other embodiments, processor 204 includes a single processor having one or more processing cores.

Millimeter-wave radar 202 includes a millimeter-wave radar sensor circuit and an antenna(s). In some embodiments, the millimeter-wave radar sensor circuit and antenna(s) are implemented in bistatic configuration (i.e., a transmitter and a receiver separated by a distance). In other embodiments, the millimeter-wave radar sensor circuit and antenna(s) are implemented in monostatic configuration (i.e., a transmitter and a receiver are collocated). Some embodiments may have one or more antennas dedicated for the transmitter (TX) module and one or more antennas dedicated for the receiver (RX) module of the millimeter-wave radar. Other embodiments may share the same antenna for the RX and TX modules of the millimeter-wave radar, such as in monostatic implementations.

The millimeter-wave radar sensor circuit may transmit and receive signals in the GHz range. For example, some embodiments may transmit and receive signals such as chirps in a band allocated around frequencies such as 95 GHz, 120 GHz, 140 GHz, and/or 240 GHz and/or other frequencies between about 95 GHz and about 240 GHz range. Other embodiments may transmit and receive signals such as chirps in the 20 GHz to 122 GHz range. Yet other embodiments may transmit and receive signals, such as chirps with frequencies above 240 GHz. Other frequencies and frequency ranges are also possible.

In some embodiments, the millimeter-wave radar sensor circuit process the echo signals received by using band-pass filter (BPFs), low-pass filter (LPFs), mixers, low-noise amplifier (LNAs), and intermediate frequency (IF) amplifiers in ways known in the art. The echo signals are then digitized using one or more analog-to-digital converters (ADCs) for further processing. Other implementations are also possible.

Composite material structure 208 may include composite materials such as, carbon fiber, fiberglass (also known as glass-reinforced plastic, glass-fiber reinforced plastic, or GFK), or aramid fiber. Other types of composite materials may be used.

Figure 3:
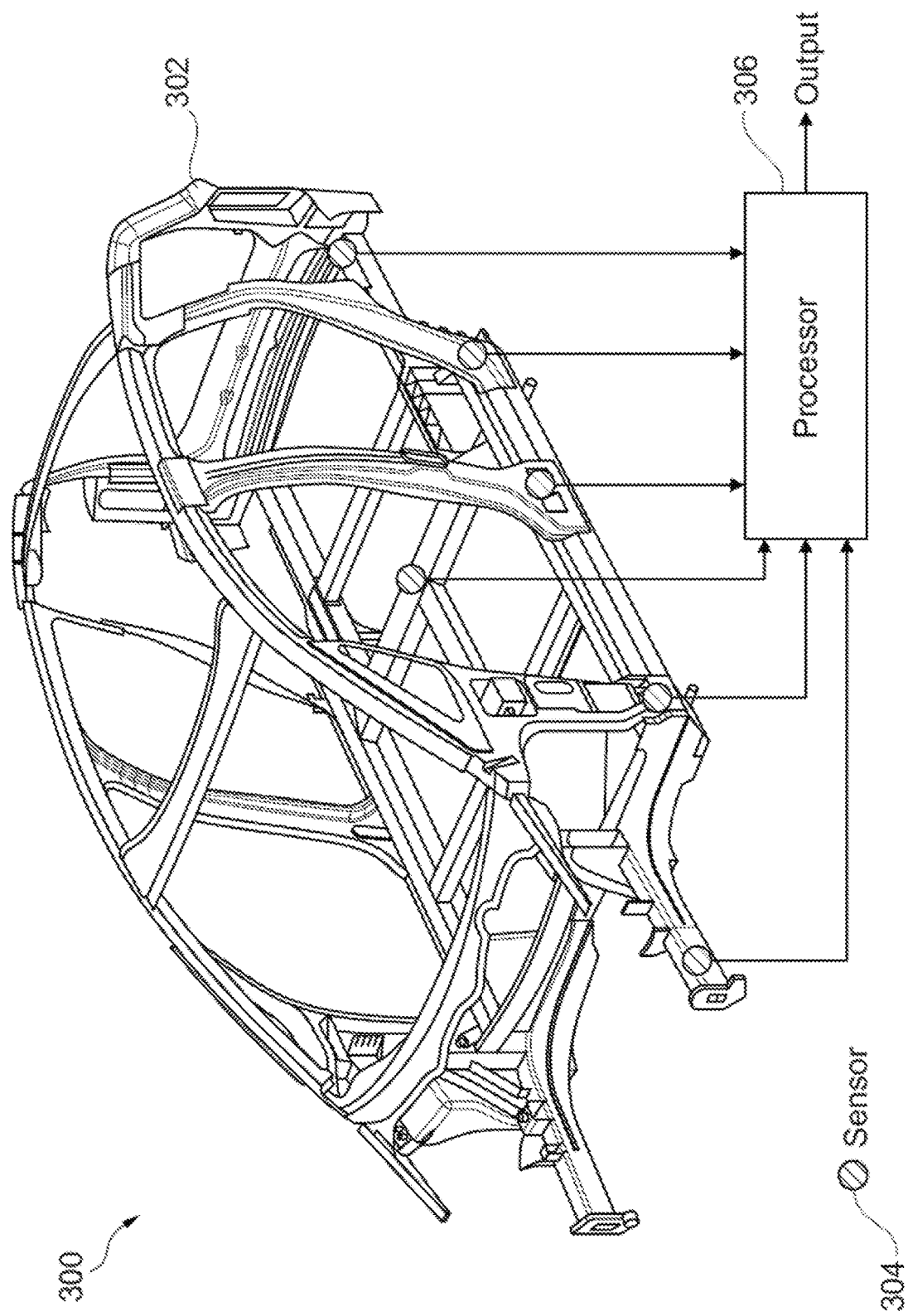
FIG. 3 shows a car frame, according to an embodiment of the present invention.

FIG. 3 shows car frame 300, according to an embodiment of the present invention. Car frame 300 includes composite material frame 302, and a plurality of sensors 304. FIG. 3 shows sensors 304 disposed on a first half of composite material frame 302 for clarity purposes. It is understood that a second half of composite material frame 302 includes a plurality of sensors 304 symmetrically disposed with respect to the first half (not shown).

The arrangement of sensors 304 in composite material frame 302 as shown in FIG. 3 is a non-limiting example of a possible arrangement. In some embodiments, sensors 304 may be disposed in composite material frame 302 in a symmetrical arrangement that is different than the arrangement shown in FIG. 3. In other embodiments, sensors 304 may be disposed in a non-symmetrical arrangement.

The number of sensors 304 of car frame 300 (11 in number) is an example of a possible number of sensors 304. A different number of sensors 304, such as more than 11 sensors, or less than 11 sensors, may be used.

Sensors 304 may be implemented, for example, with millimeter-wave radar 202. Each of the sensors 304 monitors a respective location, or region, of composite material frame 302. The location of each of the sensors 304 may be based, for example, on monitoring locations that are particularly susceptible to degradation (e.g., exposed to more stress than other locations or to a particular type of stress) or particularly critical (e.g., failure at the critical location results in catastrophic failure).

In some embodiments, sensors 304 may be embedded inside composite material frame 302 during manufacturing of the composite material frame 302. For example, sensors 304 may be fastened to composite material frame 302, and are for instance glued to composite material frame 302. In other embodiments, sensors 304 may be disposed at the surface of composite material frame 302 after composite material frame 302 is manufactured. In some embodiments, the distance between a sensor 304 and the corresponding portion of composite material is very short (e.g., less than 10 cm, or less than 1 cm, such as 1 mm). Larger distances may also be used.

In some embodiments, a calibration step is performed to determine the distance between one or more sensors 304 and their corresponding portions of composite material frame 302. In some embodiments, the distance between sensors 304 and their corresponding portions of composite material frame 302 is fixed after calibration.

Each of the sensors 304 sends the processed data indicative of whether a property change has occurred at the respective monitored location to central processor 306. In some embodiments, sensors 304 send unprocessed data to central processor 306, and central processor 306 processes the data from each of sensors 304 to determine whether a property change has occurred at the respective monitored location. A different allocation of processing tasks between sensors 304 and central processor 306 is also possible.

Central processor 306 may generate an output to alert a user (e.g., driver, or external controller) and/or report the change (or lack of change) to the user based on the data received from sensors 304. In some embodiments, central processor 306 stores the reference phase measurements and the reference average power measurements of each of the sensors 304 and receives the raw measurements from each of the sensors 304 each time each of the sensors 304 makes a measurement. In such embodiments, central processor 306 makes the determination of whether a property change of the composite material has occurred instead of the individual (local) sensors 304.

In some embodiments, central processor 306 aggregates the information from all or most of the sensors 304 to determine an overall health of composite material frame 302.

In some embodiments, central processor 306 may be the main CPU of the car, which typically monitors other functions of the car, such as engine temperature, tire pressure, etc. In other embodiments, central processor 306 may be coupled to the main CPU of the car. In yet other embodiments, central processor 306 is not coupled to the main CPU of the car.

In some embodiments, each of the sensors 304 is implemented with a monostatic implementation. Using a monostatic implementation typically has the advantage of being smaller compared to a bistatic implementation.

Since property changes of composite material frame 302 occur over long periods of time (e.g., months or years), it is possible to make measurements of the properties of composite material frame 302 with a very low duty cycle. For example, in some embodiments, each of the sensors 304 performs a measurement (e.g., transmit a GHz signal, and receives and analyzes the echo signal reflected by the respective portion of composite material frame 302) once per day or once per start of the car, or once every, e.g., two hours. Other intervals are also possible.

Measuring the property changes of composite material frame 302 with a very low duty cycle has the advantage that each of the sensors 304 can operate with very low average power consumption. In some embodiments, each of the sensors 304 operates by using energy from a battery (e.g., lithium-ion, alkaline, or other). Since energy consumption of each of the sensors 304 may be very low (e.g., due to the very low duty cycle), each of the sensors 304 may operate for a very long time (e.g., month or years) without recharging or replacing their respective local batteries. In such embodiments, wires coupled between each of the sensors 304 and the main battery of the car (e.g., the typical 12 V battery of a car) may be avoided.

In some embodiments, energy harvesting (e.g., from electromechanical radiation, solar radiation, car vibration, etc.) may be used to recharge the respective local battery that is connected to each of the sensors 304 to extend the operating life of each of the sensors 304. In other embodiments, wires are coupled between each of the sensors 304 and the battery of the car to recharge the respective local battery of each of the sensors 304 or to provide power to each of the sensors 304 directly.

In some embodiments, each of the sensors 304 may communicate with central processor 306 via wireless communication, such as by using WiFi, Bluetooth, or a communication protocol similar to or equal to communication protocols used in Tire Pressure Monitoring Systems (TPMS). By communicating via wireless communication, wires connecting each of the sensors 304 to central processor 306 may be avoided. In other embodiments, each of the sensors 304 communicate with central processor 306 using wired communication, such as by using Serial Peripheral Interface (SPI).

In some embodiments, such as embodiments that perform measurements with low duty cycle and communicate with central processor 306 using wireless communication, sensors 304 do not have wires running through composite material frame 302. For example, in such embodiments, sensors 304 may lack wires connecting sensors 304 to the main battery of the car and may lack wires connecting sensors 304 to central processor 306.

Some of the properties of composite material frame 302 may change as a result of long term stress, for instance via a process that is known as creep. For short-term stress, if the magnitude of the short-term stress is low, the properties of composite material frame 302 may temporarily change and revert back to the original condition. If the magnitude of the short-term stress is high, the properties of composite material frame 302 may change permanently.

In some embodiments, each of the sensors 304 continuously measures the phase and/or average power of the echo signal. By continuously transmitting, reflecting, and analyzing the phase and/or average power of the echo signal, it is possible to detect temporary property changes in composite material frame 302. The number of temporary property material changes may be indicative of accelerated aging of composite material frame 302. For example, in some embodiments, the magnitude of the deviation in temporary property changes that is monitored/tracked is based on a minimum deviation sufficient to cause deformations of the composite material.

Additionally, by continuously monitoring the properties of composite material frame 302, it is possible to immediately warn a user if a sudden change occurs in composite material frame 302. This is particularly advantageous in environments where composite material frame 302 is subjected to continuous, periodic, frequent or intense stress, such as in the case of an off-road vehicle, military vehicles, aircrafts having composite structures, and in industrial applications.

Figure 4:
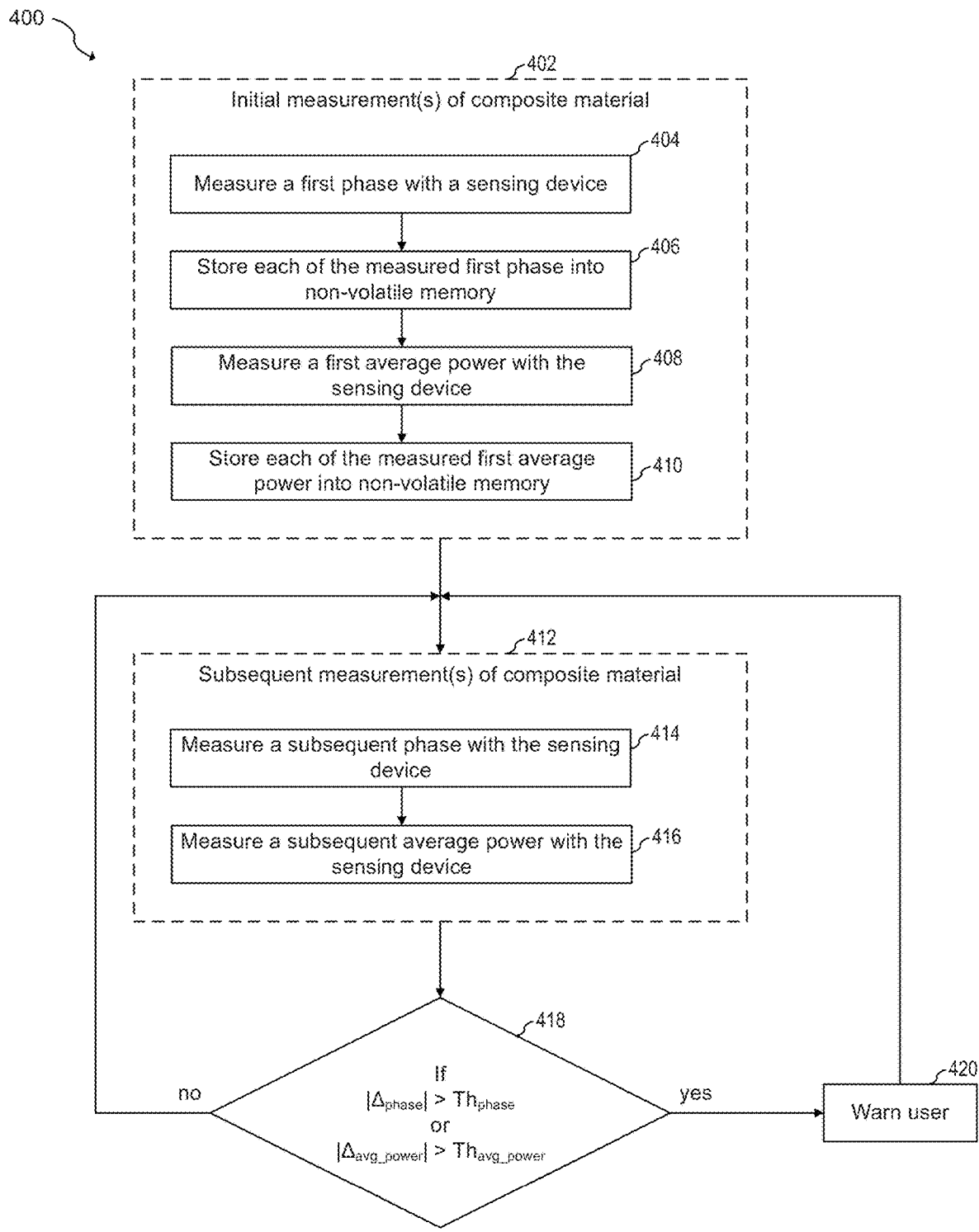
FIG. 4 illustrates a flow chart of an embodiment method for monitoring the properties of a composite material structure, according to an embodiment of the present invention.

FIG. 4 illustrates a flow chart of embodiment method 400 for monitoring the properties of a composite material structure, according to an embodiment of the present invention. Method 400 may be implemented in car frame 300. Method 400 may also be implemented in other composite material structures. The discussion that follows assumes that car frame 300 implements method 400 for monitoring the properties of a composite material structure.

During step 402, initial measurements of the properties of a composite material structure, such as composite material frame 302, are made so as to obtain the expected signal or signals to which future measurements will be compared to determine whether a property change of the structure has occurred. Step 402 may also be referred to as a calibration step. Step 402 may be performed during manufacturing or assembly of the composite material structure or at a time when monitoring of the properties of the composite material structure is to begin.

During step 404, a first phase measurement, such as described with respect to FIG. 2, is made by a sensing device, such as sensor 300 implemented with millimeter-wave radar 202. During step 406, the first phase measurement is stored in non-volatile memory inside or coupled to millimeter wave radar 202 or in a central processor or associated memory, such as central processor 306.

During step 408, a first average power measurement, such as described with respect to FIG. 2 is made by the sensing device. During step 410, the first average power measurement is stored in the non-volatile memory.

Steps 404, 406, 408 and 410 may be performed in a different order, such as 408, then 410, then 404, and then 404. Alternatively, steps 404 and 408 may be performed before steps 406 and 410. In some embodiments, steps 404 and 406 may be skipped. In other embodiments, steps 408 and 410 may be skipped. In yet other embodiments, additional parameters related to the echo signal may be measured and stored, such as frequency changes (e.g., Doppler effects) or other time domain changes.

During step 412, subsequent measurements of the properties of the composite material structure are performed so as to determine if a property change thereof has occurred. During step 414, a subsequent phase measurement is performed with the sensing device. During step 416, a subsequent average power measurement is performed with the sensing device. In some embodiments, steps 414 is performed before step 416. In other embodiments, step 416 is performed before step 414. In yet other embodiments, steps 414 and 416 are performed simultaneously. In some embodiments, step 414 may be skipped. In other embodiments, step 416 may be skipped. In yet other embodiments, additional parameters related to the echo signal may be measured, such as frequency changes (e.g., Doppler effects) or other time domain changes.

During step 418, the magnitude of the phase difference between the subsequent phase measurement and the first phase measurement is compared with a phase threshold $Th_{phase}$. If the magnitude of the phase difference is lower than the phase threshold $Th_{phase}$, step 412 is executed. If the magnitude of the phase difference is greater than the phase threshold $Th_{phase}$, a user, such as a driver of the car that includes car frame 300 or an external controller, is warned that the composite material structure may fail, during step 420.

During step 418, the magnitude of the average power difference between the subsequent average power measurement and the first average power measurement is compared with an average power threshold $Th_{avg\_power}$. If the magnitude of the average power difference is lower than the average power threshold $Th_{avg\_power}$, step 412 is executed. If the magnitude of the average power difference is greater than the phase threshold $Th_{avg\_power}$, the user is warned that the composite material structure may fail, during step 420. Step 412 is executed after step 420, repeating the sequence.

It is understood that even though method 400 was explained with respect to a single sensing device, the composite material structure may include a plurality of sensing devices, each monitoring a corresponding portion of the composite material structure.

The phase threshold $Th_{phase}$ and the average power threshold $Th_{avg\_power}$ may be different for different composite materials and composite material structures. A person skilled in the art should be able to find the specific thresholds for a particular composite material and composite material structure. For example, in some embodiments, the specific thresholds used in a particular application may be determined during a characterization step in which a test composite material structure is subjected to various stresses until the composite material structure fails (e.g., cracks) while continuously monitoring the phase and average power of the echo signal reflected by the test composite material structure.

Other embodiments may gather information from usage and use machine learning algorithms, such as a random forest algorithm, to determine failure signatures that are indicative of property changes. For example, in some embodiments, a plurality of cars may collect respective echo data. The property changes of the respective car frames may be periodically measured. The machine learning algorithm may then create signatures, based on correlation between phase changes, average power changes, Doppler effects, etc. to detect deviations in property of the composite material structure that are predictive of a mechanical mode of failure (e.g., cracking). A classifier may then be used to distinguish between relevant changes (e.g., a permanent deformation) and changes that are not indicative of potential failure, such as a temporary change in the property of the material or measurement noise.

Figure 5:
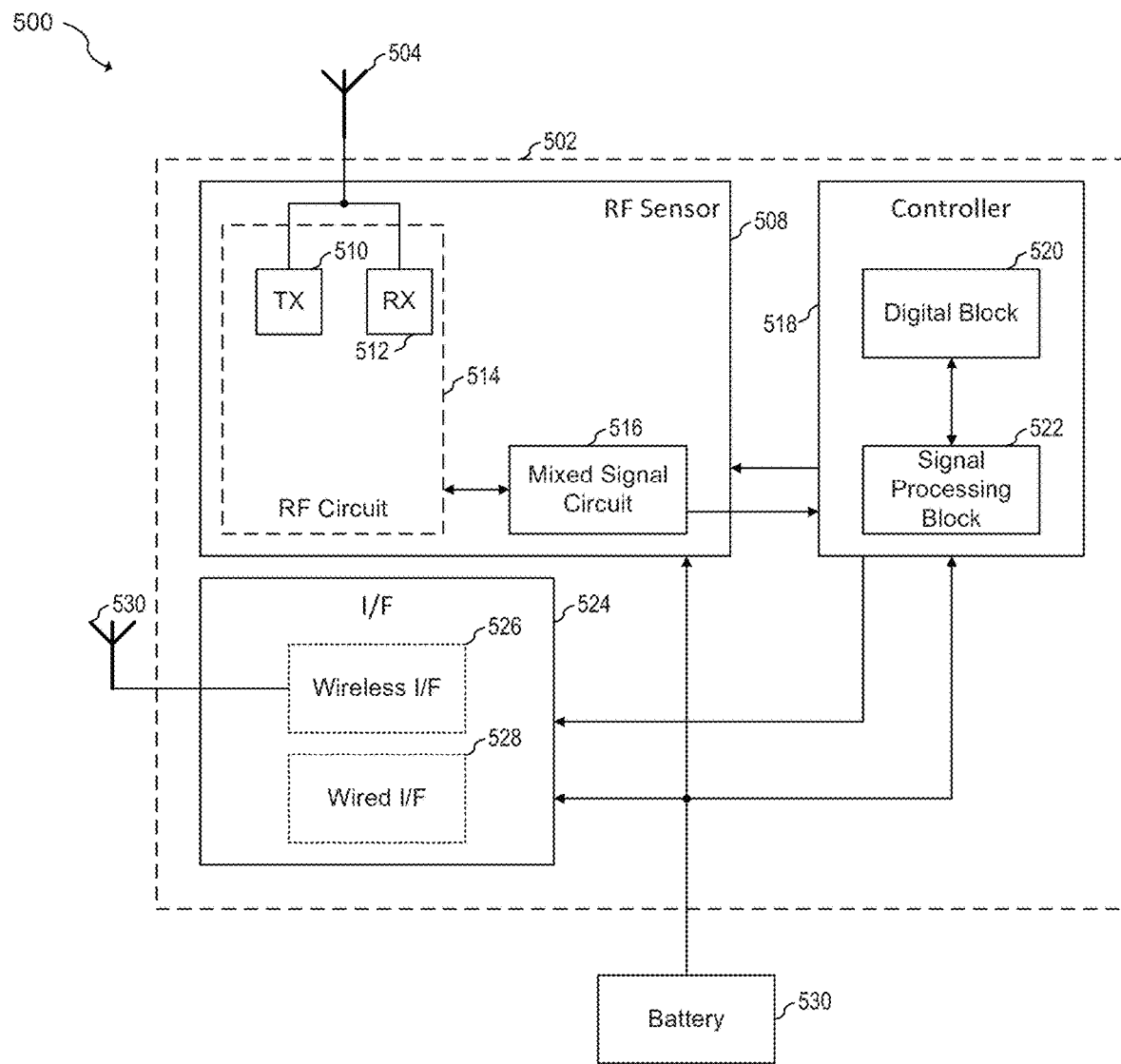
FIG. 5 shows a schematic diagram of a sensor for monitoring the properties of a composite material structure, according to an embodiment of the present invention.

FIG. 5 shows a schematic diagram of sensor 500 for monitoring the properties of a composite material structure, according to an embodiment of the present invention. Sensor 500 includes millimeter-wave radar sensor circuit 508 implemented in monostatic configuration, antenna 504, controller 518, and interface circuit 524. Millimeter-wave radar sensor circuit 508 includes radio-frequency (RF) circuit 514, and mixed signal circuit 516. Controller 518 includes digital block 520 and signal processing block 522.

RF circuit 514 is configured to transmit signals (e.g., chirps) towards a composite material structure and to receive the echo (i.e., reflection) signal from the composite material structure. RF circuit 514 includes transmitter circuit 510, receiver circuit 512. RF circuit 514 is implemented in monostatic configuration.

Transmitter circuit 510 and receiver circuit 512 may be implemented in any way known in the art. As shown in FIG. 5, in a monostatic configuration, transmitter circuit 510 and receiver circuit 512 are connected to the same antenna 504. Some embodiments may be implemented in a bistatic configuration, in which transmitter circuit 510 is connected to a first antenna and receiver circuit 512 is connected to a second antenna.

Mixed signal circuit 516 is configured to control RF circuit 514 to transmit signals (e.g., chirps), and to receive the echo signal. Mixed signal circuit 516 is also configured to translate the RF signals into digital signals that are then transmitted to controller 518.

Mixed signal circuit 516 may be implemented in any way known in the art. For example, in some embodiments, mixed signal circuit 516 includes one or more band-pass filters (BPFs), low-pass filters (LPFs), mixers, low-noise amplifier (LNA), intermediate frequency (IF) amplifiers, and ADCs.

Controller 518 is configured to process the signals received from millimeter-wave radar sensor circuit 508 and transmit it to a central processor (not shown). Controller 518 may be implemented in any way known in the art and typically includes digital block 520 for general control purposes (e.g., controlling millimeter-wave radar sensor circuit 508 and interface circuit 524) and a signal processing block 522 for processing the signals received from millimeter-wave radar sensor circuit 508. In some embodiments, signal processing block 522 is not implemented and, instead, the raw data received from millimeter-wave radar sensor circuit 508 is sent to the central processor for further processing.

Interface circuit 524 is configured to transmit data from controller 518 to the central processor. Interface circuit 524 may include wireless interface 526 and/or wired interface 528. If wireless interface 526 is implemented, wireless interface 526 is connected to antenna 530.

Wireless interface 526 may be implemented in any way known in the art. For example, wireless interface 526 may be implemented for WiFi or Bluetooth communications. Other communication protocols, including low power communication protocols and low data rate communication protocols may be used.

Wired interface 528 may be implemented in any way known in the art. For example, wired interface 528 may be implemented for SPI communications, Universal asynchronous receiver-transmitter (UART) communication or Inter-Integrated Circuit (I²C) communications. Other communication protocols may be used.

In some embodiments, millimeter-wave radar sensor circuit 508, controller 518, and interface circuit 524 are coupled to battery 530. Battery 530 may be a rechargeable battery. For example, in some embodiments, battery 530 is a rechargeable battery that is recharged by energy harvested from the environment (e.g., electromagnetic, solar, vibration, etc.).

In some embodiments, battery 530 is a non-rechargeable battery. The use of non-rechargeable batteries may be implemented, for example, in embodiments where measuring the property changes of the composite material structure is performed at a very low duty cycle.

Other embodiments do not include battery 530. In such embodiments, millimeter-wave radar sensor circuit 508, controller 518, and interface circuit 524 receive power from the main battery of the car. For example, an embodiment in which a sensor continuously monitors property changes of the composite material structure may receive power from the main battery of the car instead of implementing a local battery.

In some embodiments, millimeter-wave radar sensor circuit 508, controller 518, and interface circuit 524 are implemented inside a same package 502. Some embodiments include antenna 504 and/or antenna 530 inside package 502. Other embodiments implement each of millimeter-wave radar sensor circuit 508, controller 518, and interface circuit 524, and antennas 504 and 530 discretely in a printed circuit board (PCB).

Example embodiments of the present invention are summarized here. Other embodiments can also be understood from the entirety of the specification and the claims filed herein.

Example 1

A method for monitoring property changes in a composite material structure, the method including: transmitting a radio-frequency (RF) signal towards the composite material structure using a millimeter-wave radar sensor embedded in the composite material structure; receiving a reflected signal from the composite material structure using the millimeter-wave radar sensor; processing the reflected signal; and determining a property change in the composite material structure based on processing the reflected signal.

Example 2

The method of example 1, where determining the property change in the composite material structure includes using a classification process to determine a type of property change among a set of possible types of property changes.

Example 3

The method of one of examples 1 or 2, where processing the reflected signal includes determining a difference between the reflected signal and a predetermined expected reflected signal.

Example 4

The method of one of examples 1 to 3, further including: transmitting an initial RF signal towards the composite material structure using the millimeter-wave radar sensor; after transmitting the initial RF signal, receiving an initial reflected signal from the composite material structure using the millimeter-wave radar sensor; and determining the predetermined expected reflected signal based on the initial reflected signal.

Example 5

The method of one of examples 1 to 4, where determining the property change of the composite material structure includes determining that a property change has occurred when the determined difference is greater than a first threshold, and where the first threshold is determined during a characterization phase.

Example 6

The method of one of examples 1 to 5, where processing the reflected signal includes: determining a phase of the reflected signal; and determining a phase magnitude difference between the phase of the reflected signal and a phase reference, and where determining the property change of the composite material structure includes determining that a property change has occurred when the determined phase magnitude difference is greater than a phase threshold.

Example 7

The method of one of examples 1 to 6, where processing the reflected signal includes: determining an average power of the reflected signal; and determining an average power magnitude difference between the average power of the reflected signal and an average power reference, and where determining the property change of the composite material structure includes determining that a property change has occurred when the determined average power magnitude difference is greater than an average power threshold.

Example 8

The method of one of examples 1 to 7, where the composite material structure includes carbon fiber.

Example 9

The method of one of examples 1 to 8, further including transmitting a plurality of RF signals towards the composite material structure using the millimeter-wave radar sensor, where each of the plurality of RF signals is transmitted every two hours or slower.

Example 10

The method of one of examples 1 to 9, where the composite material structure is a frame of a car.

Example 11

The method of one of examples 1 to 10, further including transmitting a plurality of RF signals towards the frame of the car using the millimeter-wave radar sensor, where transmitting the plurality of RF signals includes transmitting an RF signal each time the car is started.

Example 12

The method of one of examples 1 to 11, where the RF signal includes a chirp.

Example 13

The method of one of examples 1 to 12, where the chirp has a frequency band around about 95 GHz, 120 GHz, 140 GHz, or 240 GHz.

Example 14

The method of one of examples 1 to 13, further including transmitting first data to a central processor, where the first data is based on the reflected signal.

Example 15

The method of one of examples 1 to 14, where the first data includes a difference between the reflected signal and a predetermined expected reflected signal.

Example 16

The method of one of examples 1 to 14, where transmitting the first data includes transmitting the first data using a wireless link.

Example 17

The method of one of examples 1 to 16, further including recharging a battery coupled to the millimeter-wave radar sensor by using energy harvesting from electromagnetic radiation.

Example 18

The method of one of examples 1 to 17, where the property change of the composite material structure includes delamination, deformation or a change in permittivity of the composite material structure.

Example 19

A system including: a plurality of sensing devices disposed in a composite material structure; and a central processor, where each sensing device of the plurality of sensing devices includes: a millimeter-wave radar sensor circuit configured to transmit a radio-frequency (RF) signal towards the composite material structure, and after transmitting the RF signal, receive an echo signal from the composite material structure, and a respective controller, where the respective controller or the central processor is configured to: process the echo signal, and determine a property change in the composite material structure based on processing the echo signal.

Example 20

The system of example 19, where processing the echo signal includes determining a difference between the echo signal and a predetermined echo signal.

Example 21

The system of one of examples 19 or 20, where the respective controller or the central processor is configured to process the echo signal by: determining a phase of the echo signal; determining an average power of the echo signal; determining a phase magnitude difference between the phase of the echo signal and a phase reference; and determining an average power magnitude difference between the average power of the echo signal and an average power reference, where the respective controller or the central processor is configured to determine the property change by determining that a property change has occurred when the determined phase magnitude difference is greater than a phase threshold, or when the determined average power magnitude difference is greater than an average power threshold.

Example 22

The system of one of examples 19 to 21, where the composite material structure includes carbon fiber.

Example 23

The system of one of examples 19 to 22, where the composite material structure is a frame of a car.

Example 24

The system of one of examples 19 to 23, where the central processor is a main central processing unit (CPU) of the car.

Example 25

The system of one of examples 19 to 24, where each millimeter-wave radar sensor circuit and the respective controller are packaged together in the same respective package.

Example 26

The system of one of examples 19 to 25, where each millimeter-wave radar sensor circuit is coupled to a respective local battery.

Example 27

The system of one of examples 19 to 26, where the respective local battery is a non-rechargeable battery.

Example 28

The system of one of examples 19 to 27, where each millimeter-wave radar sensor circuit includes a wireless interface circuit coupled to the respective controller and configured to communicate wirelessly with the central processor.

Example 29

The system of one of examples 19 to 28, where each millimeter-wave radar sensor circuit includes a transmitting antenna and a receiving antenna.

Example 30

The system of one of examples 19 to 29, where the transmitting antenna and the receiving antenna are the same antenna.

Example 31

A car including: a carbon fiber frame; a main central processing unit (CPU); and a plurality of sensing devices embedded in the carbon fiber frame, where each sensing device of the plurality of sensing devices includes: a millimeter-wave radar sensor circuit configured to: transmit a plurality of radio-frequency (RF) signals towards the carbon fiber frame, and receive a plurality of echo signals from the carbon fiber frame, and a respective controller, where the respective controller or the main CPU is configured to: process each of the plurality of the echo signals; and determine a property change in the carbon fiber frame based on processing each of the plurality of the echo signals.

Example 32

A method for monitoring property changes in a composite material structure, the method including: transmitting a plurality of radio-frequency (RF) signals towards the composite material structure using a millimeter-wave radar sensor embedded in the composite material structure; receiving a plurality of reflected signals from the composite material structure using the millimeter-wave radar sensor; processing each of the plurality of the reflected signals; and determining a property change in the composite material structure based on processing each of the plurality of the reflected signals.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. For example, although the previous examples referred to a composite material frame, embodiments may be implemented in other types of structures, such as in a composite material crane, and other industrial applications. It is therefore intended that the appended claims encompass any such modifications or embodiments.

What is claimed is:
1. A method for monitoring property changes in a composite material structure, the method comprising:
transmitting an initial radio-frequency (RF) signal towards the composite material structure using a millimeter-wave radar sensor embedded in the composite material structure, wherein a distance between the millimeter-wave radar sensor and the composite material structure is fixed;
after transmitting the initial RF signal, receiving an initial reflected signal from the composite material structure using the millimeter-wave radar sensor;
determining an initial value based on the initial reflected signal;
storing the initial value in non-volatile memory;
after storing the initial value in the non-volatile memory, transmitting a subsequent RF signal towards the composite material structure using the millimeter-wave radar sensor;
receiving a subsequent reflected signal from the composite material structure using the millimeter-wave radar sensor;
determining a difference between a subsequent value that is based on the subsequent reflected signal and the initial value; and
determining a property change in the composite material structure based on the determined difference.

2. The method of claim 1, wherein determining the property change in the composite material structure comprises using a classification process to determine a type of property change among a set of possible types of property changes.

3. The method of claim 2, wherein the property change of the composite material structure comprises delamination, deformation or a change in permittivity of the composite material structure.

4. The method of claim 1, wherein determining the property change of the composite material structure comprises determining that a property change has occurred when the determined difference is greater than a first threshold, and wherein the first threshold is determined during a characterization phase.

5. The method of claim 1, further comprising:
determining an initial phase value based on the initial reflected signal, so that the initial value is equal to the initial phase value; and
determining a subsequent phase value based on the subsequent reflected signal so that the subsequent value is equal to the subsequent phase value,
wherein determining the difference between the subsequent value and the initial value comprises determining a phase magnitude difference between the subsequent phase value and the initial phase value, and wherein determining the property change in the composite material structure comprises determining that a property change has occurred when the determined phase magnitude difference is greater than a phase threshold.

6. The method of claim 1, further comprising:
determining an initial average power value based on the initial reflected signal, so that the initial value is equal to the initial average power value; and
determining a subsequent average power value based on the subsequent reflected signal so that the subsequent value is equal to the subsequent average power value,
wherein determining the difference between the subsequent value and the initial value comprises determining an average power magnitude difference between the subsequent average power value and the initial average power value, and wherein determining the property change in the composite material structure comprises determining that a property change has occurred when the determined average power magnitude difference is greater than an average power threshold.

7. The method of claim 1, further comprising transmitting a plurality of RF signals towards the composite material structure using the millimeter-wave radar sensor, wherein each of the plurality of RF signals is transmitted every two hours or slower.

8. The method of claim 1, wherein the composite material structure is a frame of a car.

9. The method of claim 8, further comprising transmitting a plurality of RF signals towards the frame of the car using the millimeter-wave radar sensor, wherein transmitting the plurality of RF signals comprises transmitting an RF signal each time the car is started.

10. The method of claim 1, wherein the RF signal comprises a chirp that has a frequency band around about 95 GHz, 120 GHz, 140 GHz, or 240 GHz.

11. The method of claim 1, further comprising transmitting first data to a central processor, wherein the first data is based on the subsequent reflected signal.

12. The method of claim 11, wherein transmitting the first data comprises transmitting the first data using a wireless link.

13. The method of claim 1, further comprising recharging a battery coupled to the millimeter-wave radar sensor by using energy harvesting from electromagnetic radiation.

14. A system comprising:
a plurality of sensing devices disposed in a composite material structure; and
a central processor, wherein each sensing device of the plurality of sensing devices comprises:
a millimeter-wave radar sensor circuit configured to:
transmit an initial radio-frequency (RF) signal towards the composite material structure, wherein a distance between the millimeter-wave radar sensor circuit and the composite material structure is fixed,
after transmitting the initial RF signal, receive an initial echo signal from the composite material structure,
transmit a subsequent RF signal towards the composite material structure, and
after transmitting the subsequent RF signal, receive a subsequent echo signal from the composite material structure, and
a respective controller, wherein the respective controller or the central processor is configured to:
before transmitting the subsequent RF signal, determine an initial value based on the initial echo signal and store the initial value in non-volatile memory,
determine a difference between a subsequent value that is based on the subsequent echo signal and the initial value, and
determine a property change in the composite material structure based on the determined difference.

15. The system of claim 14, wherein the respective controller or the central processor is further configured to:
determine an initial phase value based on the initial echo signal, so that the initial value is equal to the initial phase value;
determine an initial average power value based on the initial echo signal;
determine a subsequent phase value based on the subsequent echo signal;
determine a subsequent average power value based on the subsequent echo signal;
determine a phase magnitude difference between the subsequent phase value and the initial phase value and determine an average power magnitude difference between the subsequent average power value and the initial average power value, wherein the respective controller or the central processor is configured to determine the property change by determining that a property change has occurred
when the determined phase magnitude difference is greater than a phase threshold, or
when the determined average power magnitude difference is greater than an average power threshold.

16. The system of claim 14, wherein the composite material structure comprises carbon fiber.

17. The system of claim 14, wherein the central processor is a main central processing unit (CPU) of a car.

18. The system of claim 14, wherein each millimeter-wave radar sensor circuit and the respective controller are packaged together in the same respective package.

19. The system of claim 14, wherein each millimeter-wave radar sensor circuit is coupled to a respective local battery.

20. The system of claim 14, wherein each millimeter-wave radar sensor circuit comprises a transmitting antenna and a receiving antenna.

21. The system of claim 20, wherein the transmitting antenna and the receiving antenna are the same antenna.

22. A car comprising:
a carbon fiber frame;
a main central processing unit (CPU); and
a plurality of sensing devices embedded in the carbon fiber frame, wherein each sensing device of the plurality of sensing devices comprises:
a millimeter-wave radar sensor circuit configured to:
transmit an initial radio-frequency (RF) signal towards the carbon fiber frame, wherein a distance between the millimeter-wave radar sensor circuit and the carbon fiber frame is fixed,
after transmitting the initial RF signal, receive an initial echo signal from the carbon fiber frame,
transmit a plurality of subsequent RF signals towards the carbon fiber frame, and
receive a plurality of echo signals from the carbon fiber frame, and
a respective controller, wherein the respective controller or the main CPU is configured to:
before transmitting the subsequent RF signal, determine an initial value based on the initial echo signal and store the initial value in non-volatile memory,
determine a respective difference between each subsequent value that is based on a respective subsequent echo signal and the initial value, and
determine a property change in the carbon fiber frame based on each of the respective differences.

23. The method of claim 1, further comprising:
transmitting a plurality of subsequent RF signals with the millimeter-wave radar sensor;
receiving a plurality of subsequent reflected signals using the millimeter-wave radar sensor, wherein the received plurality of subsequent reflected signals correspond to the transmitted plurality of subsequent RF signals;
for each of the received plurality of subsequent reflected signals, determining a respective difference between a respective subsequent value that is based on a respective subsequent reflected signal of the received plurality of subsequent reflected signals and the initial value; and
determining a property change in the composite material structure based on one or more of the respective determined differences.

24. The method of claim 23, wherein determining the property change in the composite material structure based on the one or more of the respective determined differences comprises:
determining a number of temporary property changes based each of the respective determined differences; and
determining the property change in the composite material structure based on the determined number of temporary property changes.

25. The system of claim 14, wherein each millimeter-wave radar sensor circuit comprises a respective non-volatile memory, and wherein the respective controller is configured to store the initial value in the respective non-volatile memory.

* * * * *